United States Patent [19]
Schwartz et al.

[11] Patent Number: 6,152,137
[45] Date of Patent: Nov. 28, 2000

[54] PLIABLE AND RESILIENT SEALING PAD

[76] Inventors: Alan N. Schwartz, 19211 93rd Pl. W., Edmonds, Wash. 98020; Thomas D. Theisen, 434 NE. Maple Leaf Pl., Seattle, Wash. 98115

[21] Appl. No.: 09/090,717

[22] Filed: Jun. 4, 1998

Related U.S. Application Data

[63] Continuation-in-part of application No. 08/794,154, Feb. 3, 1997, which is a continuation of application No. 08/377,257, Jan. 23, 1995, abandoned.

[51] Int. Cl.$^7$ .................................................... A61F 13/00
[52] U.S. Cl. .................................. 128/846; 2/429; 2/430; 2/428
[58] Field of Search ............................... 2/428, 430, 429, 2/439, 447, 206.25, 206.26; 128/846

[56] References Cited

U.S. PATENT DOCUMENTS

| | | |
|---|---|---|
| 3,725,953 | 4/1973 | Johnson et al. . |
| 4,369,284 | 1/1983 | Chen . |
| 4,665,570 | 5/1987 | Davis . |
| 4,707,863 | 11/1987 | McNeal . |
| 5,093,940 | 3/1992 | Nishiyama . |
| 5,331,691 | 7/1994 | Runckel . |
| 5,334,646 | 8/1994 | Chen . |
| 5,647,357 | 7/1997 | Barnett et al. . |

OTHER PUBLICATIONS

Barracuda The Best Swim Goggles packaging.
Parker Laboratories, Inc., Aquaflex® Ultrasound Gel Pad sales literature, 1991.
3M Health Care sales brochure, *Just plain talk about the many uses of Tegaderm™ transparent dressing*, 1990.

*Primary Examiner*—Michael A. Brown
*Assistant Examiner*—Lalita M. Hamilton
*Attorney, Agent, or Firm*—Thomas D. Theisen

[57] ABSTRACT

A sealing pad (14) made of a compliant and resiliently deformable gelatinous elastomer suitable to conform under pressure to form a substantially airtight seal with at least a portion of the user's skin adjacent to the sealing pad (14). The gelatinous elastomer may be attached to a second material by incorporating the gelatinous elastomer into a large plurality of interstitium in the second material. In addition, the second material can be configured to form an endoskeleton or exoskeleton that modifies the physical properties of the gelatinous elastomer.

51 Claims, 11 Drawing Sheets

PLIABLE AND RESILIENT SEALING PAD

RELATED APPLICATION

This application is a continuation-in-part of prior application Ser. No. 08/794,154, filed Feb. 3, 1997, now on appeal, which is a file wrapper continuation of prior application Ser. No. 08/377,257 filed on Jan. 23, 1995, now abandoned, priority from the filing date of which is hereby claimed under 35 U.S.C. § 120.

FIELD OF THE INVENTION

The invention relates to a pliable and resilient sealing pad for isolation of the user's skin from the outside environment and a method for attaching a gelatinous elastomer which may be used in such pad.

BACKGROUND OF THE INVENTION

It is frequently desirable to isolate all or a portion of the user's skin from the outside environment, either to isolate the skin itself or to isolate an orifice such as the user's ears, eyes, nose or mouth. Such isolation may need to be either airtight or watertight, and such terms are used interchangeable herein. Goggles provide an example of the types of problems encountered in the prior art regarding such isolation. Goggles are commonly used to separate or isolate the eyes and face of the user from the nearby environment. For example, swimming goggles are utilized to separate and protect the eyes from water thereby allowing the swimmer to see clearly within and find a path through the water. Other goggles, such as protective goggles, are utilized to prevent exposure of the user's eyes to toxins or contaminated material, such as blood or harmful gases or materials. Goggles may also be used to protect the eyes from harmful or undesirable environmental conditions, such as cold or dry air or sand or dust in the air. Goggles may also be used to retain a particular fluid or gas near the eyes.

Traditionally, goggles have been made with a rigid or semi-rigid frame, which was directly compressed against the skin of the face by use of an elastic strap extending around the user's head. Frames were poorly compliant and did not conform well to the user's face at a comfortable pressure. This often resulted in an incomplete seal that was not watertight. In order to create a better seal, the goggles could be more firmly compressed against the face. This created discomfort and irritation to the face, facial bones, and delicate underlying blood vessels.

The problem with rigid or semi-rigid frames was partially solved by utilizing softer frame materials and by placing a pad or gasket between the frame and user's face. These pads were made with various materials, such as rubber or plastic, which were softer and more compliant than the frame materials.

There are, however, problems with existing goggles that utilize a pad or gasket. Existing solid pads have limited ability to conform to the variations in the human facial bone structure. To create a watertight seal, large compressive forces often must be applied to the frame to force the existing solid pad against the user's face. In some individuals, the pressure and resulting compression can be tolerated, but in others their skin is too delicate to comfortably withstand the large compressive force required. For these individuals, discomfort precludes their ability to successfully use this form of goggles. For other individuals, the bone structure is not compatible with the shape of goggles and water and air leaks occur even with high compressive forces.

Less rigid pads or gaskets made of foam rubber or other foam plastics have also been used. These pads consist of plastic or rubber material that contains numerous tiny air spaces and can be readily compressed at low pressure. The foam pad is better able to conform to the facial bone structure. Although foam pads are generally an improvement over existing solid pads, there is a limited capacity for the foam pads to conform to the delicate facial skin and bone structures. Moreover, the compressive forces are not symmetrically distributed throughout the pad. This results in pressure points where prominent facial bones meet the pad. If the pad does not conform fully to the contour of the facial bones, the result is a leak where air, water or other material may pass between the pad and the user's face. Such leaks can often, but not always, be reduced or eliminated by increasing the pressure applied by the frame upon the face. If the foam is thick enough and enough pressure is applied, the foam pad will usually fill in the gaps between the face and frame. When tightly compressed against the face, however, the foam pad takes on more of the characteristics of a soft rubber of plastic pad. Therefore, these foam pads suffer from many of the same limitations of discomfort and damage to the facial skin and blood vessels as do the more rigid solid pads.

In addition, because foam has air pockets or pores, it cannot be fully cleaned after each usage. As a result, bacteria and fungus grow in the air pockets in the foam. Such bacterial and fungal growth can serve as a source of eye and skin infections and can be a hygiene and health risk.

Attempts have been made to vary the shape and size of the frame of goggles in order to obtain a more successful seal with the user's face. This has been useful for some individuals, but because of the human variability in facial bone structure, this is unsuccessful for many individuals. There are a limited number of shapes that can be cost-effectively manufactured and these shapes do not necessarily conform to the numerous variations in bone and facial structure.

The above-described problems with prior art goggles are illustrative of the problems inherent in creating an airtight or watertight seal over a portion of the user's skin. The previous devices used to form such seal normally result in (a) discomfort to the user due to the amount of pressure applied, (b) a seal that is not consistently and reliably airtight or watertight, or (c) an ordinarily expensive sealing mechanism.

SUMMARY OF THE INVENTION

The present invention is a sealing pad that includes a compliant and resiliently conformable gelatinous elastomer that forms an airtight or watertight seal to the user's skin under slight to moderate pressure.

The sealing pad of the invention more readily conforms to the numerous variations in topography of the user's skin when in use and returns to its original shape after use. The material of the pad will, for example in goggles, conform to the facial bone structure and form an airtight or watertight seal with less pressure or compressive force than is required for solid or semisolid frame without such a pad.

The material of the pad will also conform to the topography and structure of the users skin by distributing the compressive force throughout a larger portion of the pad. As a result, facial or other prominences will not become pressure points since the pressure is more evenly distributed within the transition pad itself. This has a potential to reduce irritation and discomfort of the sealing pad to individuals with sensitive skin. It also reduces the discomfort to an individual who has areas of bone prominence in or near the eye socket or at other locations.

Because the pad is soft and compliant, it can also more accurately contour and conform to the topography and structure of the user's skin and have the advantage of creating a more effective watertight seal than solids or foam. For example, such pads can therefore keep water out more effectively. They also can, because of the better seal, better protect the skin from dangerous environmental exposures, toxins, chemicals, gases, or contaminated blood. Because the pad is soft and compliant it can also expand and contract and be designed to absorb shock more effectively, thus protecting the eye, the eye socket, and other structures from direct compressive blow, such as might occur with sporting injuries.

Because of the pad, many shapes of covering material can be used. For example, the covering material for goggles can be a frame designed in forms that conform to the eye socket, or it can extend outside of the eye socket. The advantage of creating a frame that is not restricted to the eye socket is that the skin is thicker and less delicate over the cheek and eyebrow than it is immediately over and around the eye, resulting in greater comfort and less damage to the delicate skin of the eye. Because of the pad, the goggles require less compressive force and the compressive force need not be applied perpendicular to the frame. Thus, a non-rigid frame can be used.

Because the pad does not rely upon air holes for its malleability and contouring as is necessary with foam pads, the pad can be made and formed to be resistant to bacterial or fungal growth. A membrane that is biocompatible with the skin and which is bacterial and fungal resistant can also be placed around the transition pad. This can provide an added safety element to the pad.

The goggles can be constructed such that the components can be interchangeable and replaceable: that is, the frame, the eyepiece, the pads, and the straps could all be replaceable if damaged. This allows the user and manufacturer to produce components to the goggles that can be repaired, replaced, changed for design purposes, all at a cost less than replacing the entire goggles.

The use of a gelatinous elastomer as a sealing gasket to the user's skin that takes advantage of various unique characteristics of a gelatinous elastomer, including its ability conform to the topography of the user's skin, the consistent resiliency of the material, the inherent tackiness of the material when appropriately formulated, and the internal strength of the material.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENTS

Figure 1:
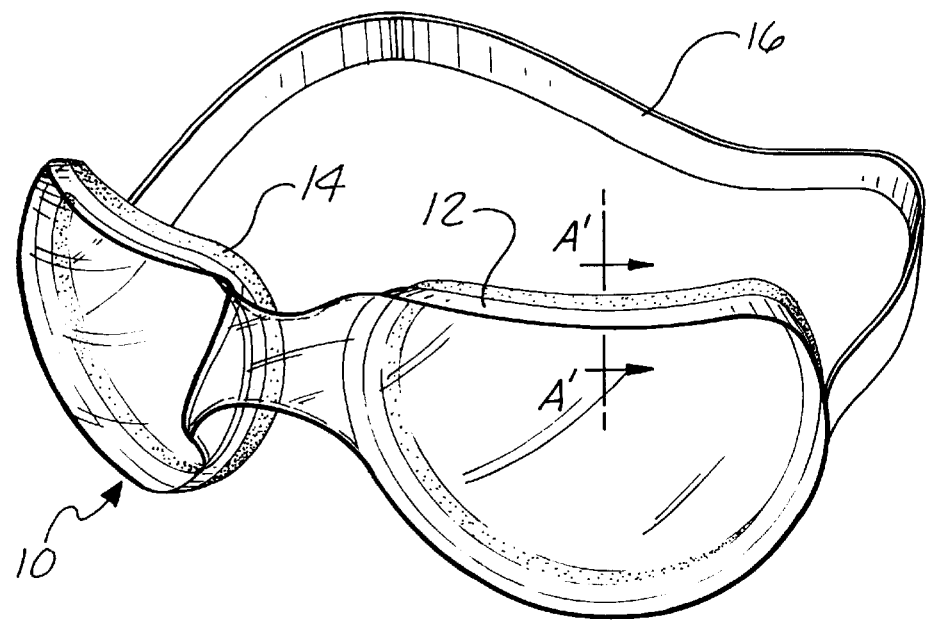
FIG. 1 shows a pictorial view of the goggles in accordance with the present invention.

Goggles 10 constructed in accordance with the present invention are shown in FIG. 1. The goggles include a frame 12 having a portion to cover, or otherwise isolate from the outside environment, one or both of the user's eyes. A portion of the frame 12 is transparent, meaning that it allows some light to pass from the outside environment to the user's eye. The transparent portion of the frame 12 may transmit all wavelengths of light, selectively block or attenuate certain wavelengths of light or attenuate all wavelengths of light.

In the preferred embodiment of the invention, the frame 12 is made of plastic or other material that is relatively rigid, yet soft enough to conform to the overall shape of the user's face and head. The frame may be made of various materials, such as rigid polyvinyl chloride, or acrylic lenses surrounded by a flexible polyvinyl chloride perimeter, for example. However, this invention is consistent with, and includes, virtually any type of frame 12 which can isolate or protect the user's eyes from the outside environment and includes, for example, rigid pieces of plastic designed to fit and generally conform to the shape of the orbit of the user's eye socket or a thin film of flexible material sized to extend beyond and fit outside the orbits of the user's eye socket.

The goggles also include a sealing pad 14 between the frame 12 and the user's face that forms a substantially airtight seal between the frame 12 and the user's face. In the preferred embodiment, the sealing pad 14 is a strip of material with a cross section width and height of between approximately one-eighth inch and approximately one-half inch. The sealing pad 14 is near at least a portion of the perimeter of the frame 12, and in the preferred embodiment entirely surrounds each of the user's eyes near perimeter of the frame. An optional strap 16 is used in the preferred embodiment to apply slight pressure to hold the sealing pad 14 against the user's face.

The sealing pad 14 is configured so that when it is in use it forms a continuous and substantially airtight seal with the user's face along at least a portion of the frame 12. The sealing pad 14 is made from a gelatinous elastomer that is both compliant and yet resiliently deformable. Specifically, the gelatinous elastomer must be sufficiently compliant to conform to the irregularities of the user's face when slight to moderate pressure is applied to the sealing pad 14. If the gelatinous elastomer is too hard or rigid, it will not form a substantially airtight seal to the user's face without the application of undue pressure resulting in pain or discomfort to the user. On the other hand, if the gelatinous elastomer is too soft, it is possible that in forming a substantially airtight seal the elastomer will be forced out from between the frame 12 and the user's face at certain locations, again, possibly causing pain or discomfort to the user or impinging on the user's eye.

The gelatinous elastomer also needs to deform in a substantially resilient manner as pressure is applied to the sealing pad 14. If the gelatinous elastomer is permanently deformed to a substantial extent when sufficient pressure is applied to form a substantially airtight seal between the sealing pad 14 and the user's face, or if the elastomer does not return to its approximate original shape following the removal of such pressure, then the goggles may not fit as well when they are used again. For example, if the goggles are used by a different user or at a slightly different location on the original user's face, any substantial permanent deformation of the elastomer may adversely affect the performance of the sealing pad 14.

Various gelatinous elastomers were evaluated for use in the sealing pad 14. The preferred embodiment of the invention is made from the same material used in the Kitecko Ultrasound Standoff Pad 3520 and 3530, manufactured by 3M Corporation of St. Paul, Minn. Various soft urethane gels and soft silicone gels were also found to be acceptably compliant and deformable, but may require the use of a membrane to prevent damage to the user's skin.

Figure 2:
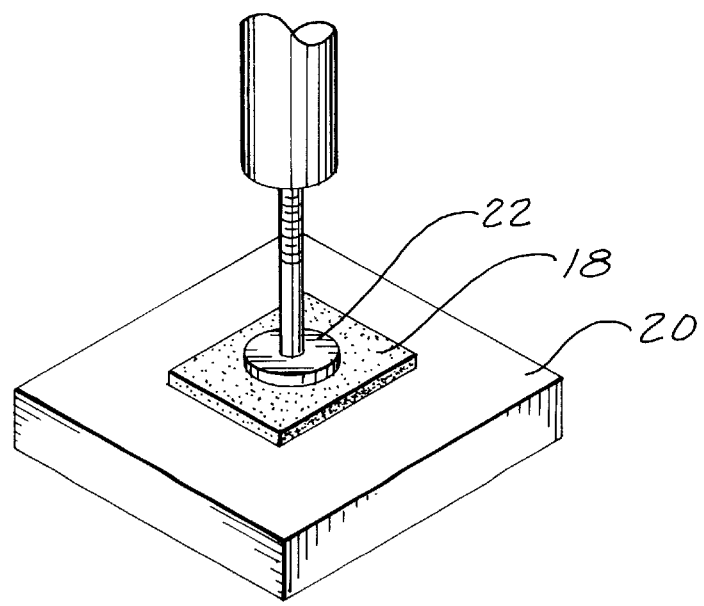
FIG. 2 shows a partial pictorial view of the apparatus used to identify whether a particular gelatinous elastomer is desirable for use in this invention.

It appears that there is no general accepted test or method to measure how compliant or deformable a gelatinous elastomer is. The following method and procedure illustrated in FIG. 2 was used to help identify whether a particular gelatinous elastomer is desirable for use in the sealing pad of this invention. A sample strip 18 of the elastomer approximately 0.3 of an inch high, 0.5 of an inch wide, and 1.0 inches long was placed upon a scale 20 that measures the downward force exerted by the sample strip 18 of gelatinous elastomer.

A rigid circular disk 22 having a diameter of 0.43 inches was placed so that it just contacted the top surface of the sample strip 18, and the scale 20 was zeroed. The rigid circular disk 22 was then moved downward in 0.025-inch increments until the sample strip 18 ceased to be resiliently deformable, i.e., until the sample started to tear under the rigid circular disk 22. For each incremental 0.025-inch deflection, the total downward force in grams measured by the scale 20 was recorded. Sample strips of gelatinous elastomers of varying compliance and resiliency (hereinafter samples A, B, D and E) made from common household edible gelatin, along with a sample cut from the Kitecko Ultrasound Standoff pad (sample C), were tested. The downward force, measured on the scale 20 in grams, for each incremental 0.015-inch deflection and for each of five samples (A–E) are set forth in the following table:

|           | A     | B      | C      | D       | E       |
|-----------|-------|--------|--------|---------|---------|
| 0.025 in. | 5 g.  | 5 g.   | 15 g.  | 20 g.   | 45 g.   |
| 0.050 in. | 10 g. | 10 g.  | 40 g.  | 75 g.   | 180 g.  |
| 0.075 in. | 15 g. | 20 g.  | 55 g.  | 125 g.  | 500 g.  |
| 0.100 in. | 20 g. | 30 g.  | 100 g. | 170 g.  | 770 g.  |
| 0.125 in. | 30 g. | 40 g.  | 195 g. | 270 g.  | 970 g.  |
| 0.150 in. | 45 g. | 55 g.  |        | 390 g.  | 1500 g. |
| 0.175 in. | 70 g. | 75 g.  |        |         | 1900 g. |
| 0.200 in. |       | 140 g. |        |         | 2600 g. |

The softest sample, sample A in the above table, is believed to represent about the most compliant, least resilient material desirable for use in a homogenous pad of the invention. Similarly, the hardest sample, sample E in the above table, is believed to represent about the least compliant, most resilient material desirable for use in the present invention. Therefore, although the invention is not necessarily limited to gelatinous elastomers with hardnesses ranging from sample A to sample E, such elastomers are considered more desirable for use in the present invention, with the most desirable material, sample C in the above table, corresponding to the material used in the Kitecko Ultrasound Standoff Pad of the preferred embodiment. Based upon the above-described measurements, it is anticipated that the gelatinous elastomer is sufficiently compliant when a compressive pressure between 100 grams per square inch and 3500 grams per square inch applied to the top surface of a thin strip of gelatinous elastomer will compress the height of the strip by-approximately 25 percent. The preferred gelatinous elastomer shows such compression at approximately 380 grams per square inch.

Due to the absence of any established test to determine the hardness or softness of a gelatinous elastomer, it must be recognized that the above results are approximations reflecting the desirable range of physical properties and are expected to have a margin of error of at least 20%. Moreover, the physical characteristics described herein were found to be proportionally applicable to strips between 0.1 inches and 0.6 inches high. It is also expected that the above physical characteristics will be applicable proportionally to different-sized samples of the gelatinous elastomer that are not precisely 0.3 inches high, so long as the relative dimensions of the different-sized samples are similar to the tested samples.

In the preferred embodiment of the present invention, the sealing pad 14 has a thin distortable membrane 24 that covers at least a portion of the gelatinous elastomer. This membrane is a smooth and regular external surface. In the preferred embodiment, the membrane is made from Tegaderm® HP Transparent Wound Dressing manufactured by the 3M Corporation of St. Paul, Minn., and is formed to create a closed torrid that encloses the gelatinous elastomer in an airtight manner. However, virtually any thin flexible film can be used for this membrane, including a film that forms on or as part of the surface of the gelatinous elastomer. In an alternative embodiment, the sealing pad 14 is used without any membrane between the sealing pad 14 and the user's skin to take advantage of the physical characteristics of the gelatinous elastomer. For example, the previously described Kitecko Ultrasound Standoff Pad manufactured by 3M Corporation is sufficiently tacky to adhere to the user's face. In another embodiment, an adhesive can be applied to the sealing pad 14. This allows the sealing pad 14 to maintain an airtight seal between the user's face and the frame 12 with little or no pressure applied to the sealing pad 14.

The sealing pad 14 can be permanently attached to the frame 12 using any one of a number of commonly known techniques, such as adhesives or physical fasteners. Alternatively, the sealing pad 14 can be removably attached to the frame 12, allowing for easy replacement of the sealing pad 14 after it is worn or damaged, using various commonly known methods, such as the methods described below.

Figure 3:
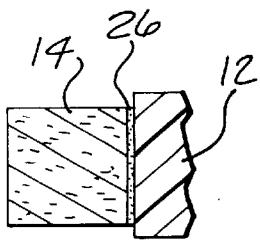
FIGS. 3–13 show partial cross sections of alternative embodiments of the goggles frame and seal suitable for use in the present invention taken along Line A-A' of FIG. 1.
Figure 4:
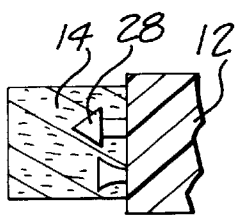
Figure 5:
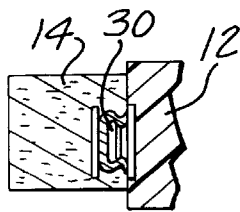
Figure 6:
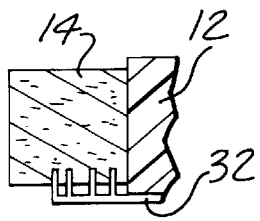
Figure 7:
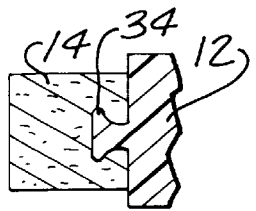
Figure 8:
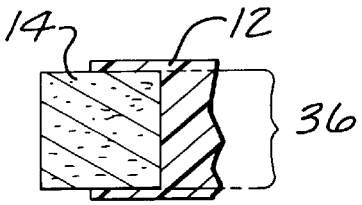
Figure 9:
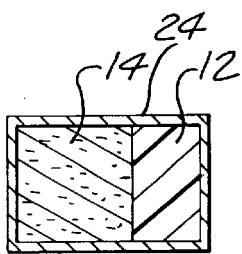
Figure 10:
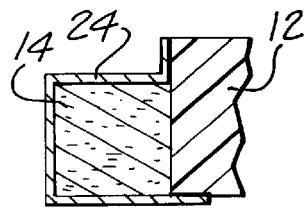
Figure 11:
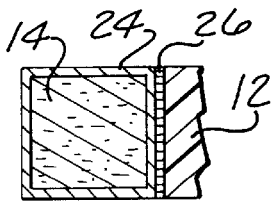
Figure 12:
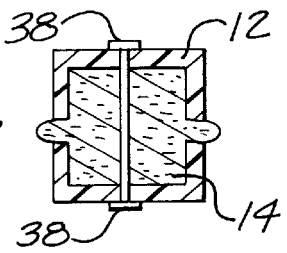
Figure 13:
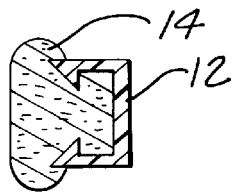

There is a multitude of means by which the sealing pad 14 can be permanently or removably attached to the frame 12. For example, the sealing pad 14 can be glued, pasted, formed and cured, or attached with adhesives 26 onto the frame 12 as shown, for example, in FIG. 3. The sealing pad 14 may also be attached using one or more pegs, anchors, screws or other fasteners 28 that are attached to the frame 12 and penetrate into the sealing pad 14 as shown, for example, in FIG. 4. The sealing pad 14 can also be attached to the frame 12 using interlocking molded forms, such as snaps 30, side projections 32, ziplock channels, or buttons 34 that are either attached to or are integral with the frame 12 and sealing pad 14 as shown, for example, in FIGS. 5–7. The sealing pad 14 may also fit into a slot or channel 36 in the frame 12 as shown, for example, in FIG. 8. The sealing pad 14 may also be attached to the frame 12 by use of a thin distortable membrane 24 that surrounds at least a portion of the frame 12 and a portion of the sealing pad 14 as shown, for example, in FIG. 9. Likewise, a membrane 24 which either partially or fully surrounds the sealing pad 14 can be attached to the frame 12 in numerous well known ways, including the use of screws, clamps, pegs, pins, glues, wires, paste, curing agents, snaps, buttons, anchors, or interlocking molded forms, as illustrated, for example, in FIGS. 10–11. The gelatinous elastomer of the sealing pad 14 can also be squeezed or compressed between two portions of the frame 12, as illustrated, for example, in FIG. 12 using a screw 38 to squeeze the elastomer. The gelatinous elastomer can also be squeezed or fastened into a channel 36 as shown, for example, in FIG. 13.

In another alternative embodiment, the pliability or softness of the sealing pad 14 varies between the frame 12 and the user's face. For example, using well-known techniques of manufacturing silicone elastomers, the sealing pad 14 may be made softer or more pliable near the user's face and be made to increase in hardness and become less pliable closer to the frame 12. This alternative embodiment can be used to provide for a very soft and flexible portion of the sealing pad 14 near the user's face while ensuring that the pad as a whole is not so deformable as to allow the frame 12 to impinge upon the user's face.

Figure 14:
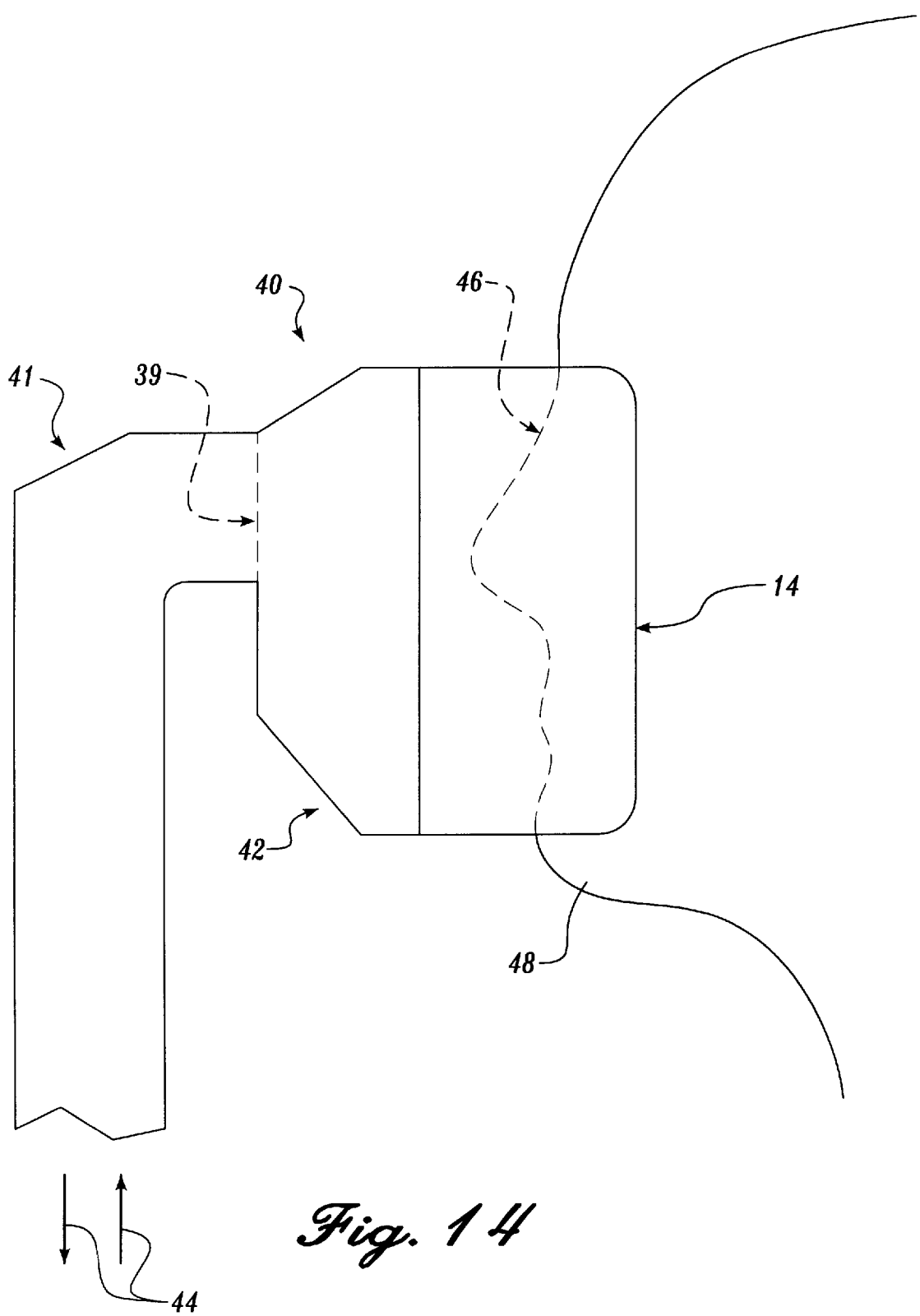
FIG. 14 is a partial pictorial view of a breathing mask utilizing the present invention.

The sealing pad 14 described in this invention can be used in other situations where it is desirable to form a substantially airtight seal with the user's skin. For example, as shown in FIG. 14, the sealing pad 14 of this invention can be used on breathing masks 40 and other apparatus designed to either partially or completely isolate any portion or portions of the user's face 46 from the outside environment. The sealing pad 14 may be used by humans and other animals.

In one embodiment, a breathing mask is composed of an annular gel sealing pad 14 that forms an airtight seal with the face and completely isolates any portion or portions of the user's face 46 from the outside environment. One example of said breathing mask composed of an annular gel sealing pad 14 is a respiratory mask 40 shown in FIG. 14 which contains at least one opening 39. Said opening 39 is coupled to a conduit 41 that can deliver and remove a gas 44 or other material. The sealing pad 14 can isolate those portions of the face that include but are not restricted to the mouth, the nose or a combination of both the mouth and nose. In FIG. 14 the embodiment shows a breathing mask with the sealing pad 14 that isolates the mouth and nose. Breathing masks 40 that isolate portions of the user's face can be used for medical applications and include but are not restricted to respirator masks, continuous airway pressure masks, and anesthesia and gas delivery masks. Other forms of masks 42 that isolate portions of the user's face related to breathing used for safety include but are not restricted to smoke inhalation prevention masks, environmental safety, and surgical masks. Breathing masks that may isolate portions of the user's face that are used for recreation include but are not restricted to aroma and scent delivery and scuba and snorkeling masks.

Figure 15:
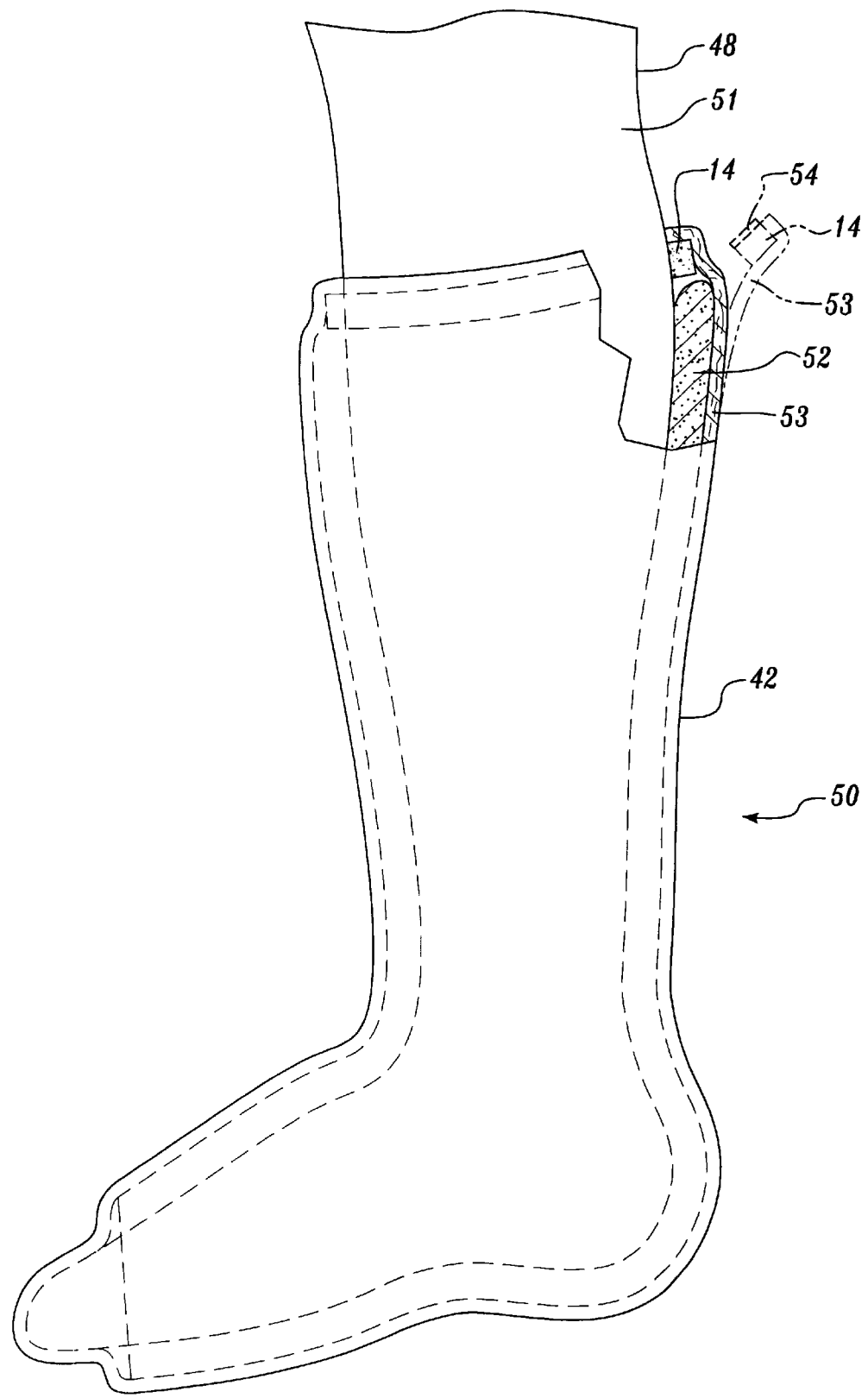
FIG. 15 is a partial pictorial view of a cast cover utilizing the present invention.
Figure 16:
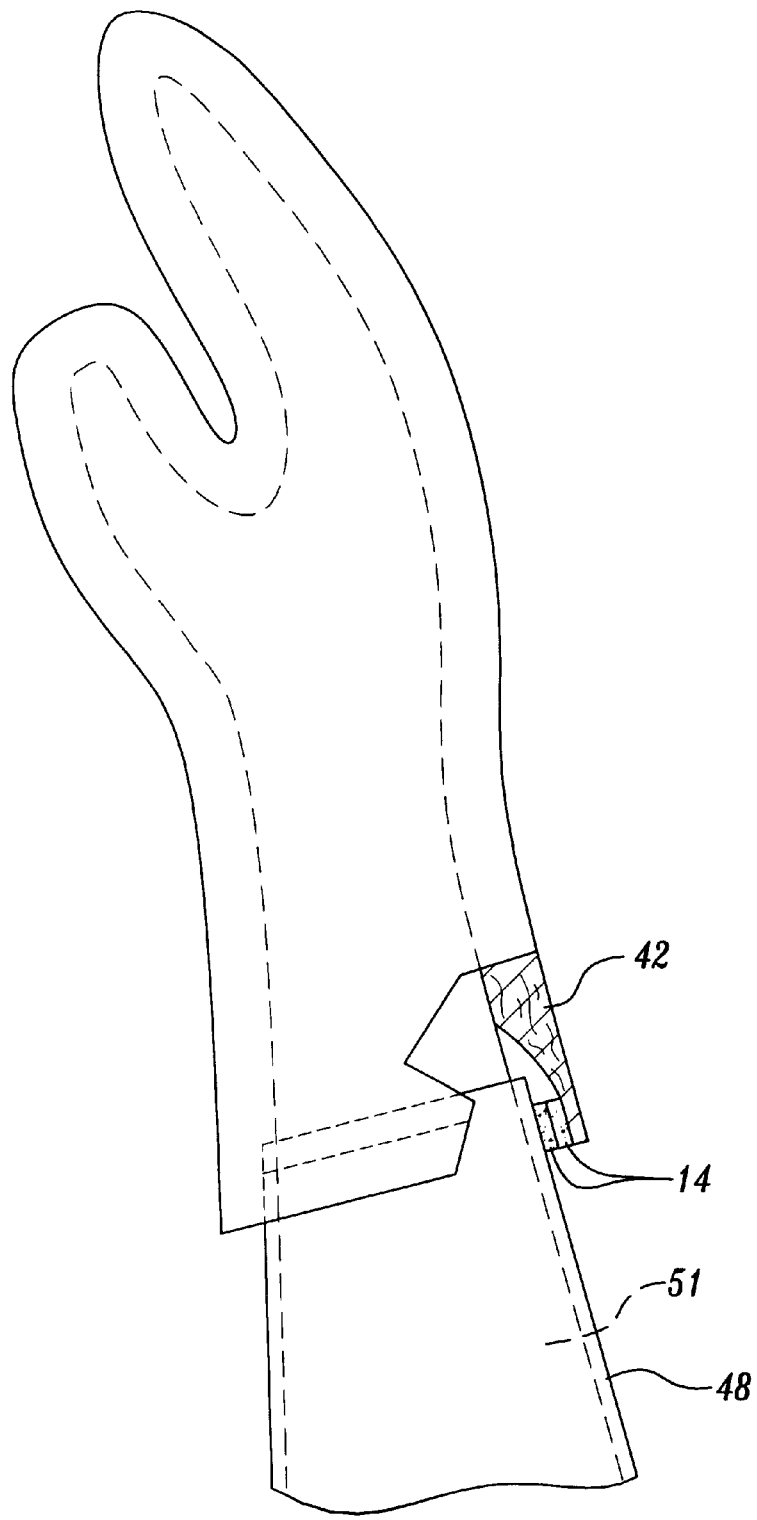
FIG. 16 is a partial cross section view of a glove and jacket sleeve utilizing the present invention.

Shown in FIGS. 15 and 16, the sealing pad 14 of this invention may be used to form an airtight or watertight seal between the user's skin 48 and skin covering material 42 such as protective clothing, garments, or drapes. In such cases, the sealing pad 14 may be forced against the user's skin 48 by the mask or garment or the sealing pad 14 may be sufficiently tacky to adhere to the user's skin 48 or another sealing pad 14 once it is initially conformed to the skin.

The sealing pad 14 of the present invention forms an airtight or watertight seal to the user's skin 48 either without the application of any pressure perpendicular to the surface of the skin or with the application of slight to moderate pressure in such direction. The sealing pad 14 of the present invention can thus be used to cover or isolate a portion of the user's skin from the outside environment either by covering the entire portion of the skin to be so isolated with the sealing pad, or by being applied along the perimeter of such portion between the user's skin 48 and a skin covering material 42 as shown in FIGS. 15 and 16. The shape of the portion of the user's skin 48 to be isolated can be of any desired shape including, but not limited to, a circle, an oval, a crescent, or a trapezoidal shape. When the sealing pad 14 is so used to isolate a portion of the user's skin 48, it can be retained against the user's skin 48 by various methods, including the inherent tackiness of the gelatinous elastomer or external pressure applied to the sealing pad 14 itself or applied through skin covering material 42 or any other material in contact with the sealing pad.

The sealing pad 14 can be directly or indirectly affixed to virtually any skin covering material 42. The skin covering material 42 can be of virtually any form or shape. For example, one embodiment illustrated in FIG. 15 and 16 consists of an airtight or watertight skin covering material 42 shaped like a bag 50 that is configured in a geometric shape such as a cone, cylinder, or other shape closed at one end and open at the other end. The skin covering material 42 can also be configured in a shape to contour or mimic a human body part or appendage 51 such as a foot-shaped sock shown in FIG. 15 or a hand-shaped glove shown in FIG. 16. The sealing pad 14 can be affixed to the skin covering material 42 at the open end to form an airtight or watertight seal with the user's skin 48.

The sealing pad 14 combined with the skin covering material 42 will then form an airtight or watertight seal around an appendage 51 when the sealing pad 14 contacts with the user's skin 48. Because of its conformability, resiliency and tackiness, the airtight or watertight seal will be complete at the portion of skin 48 in contact with the sealing pad 14. Again, pressure can be exerted on the sealing pad 14 by external devices that can include but are not restricted to using air pressure, elastic and non-elastic ties or straps, Velcro buttons, or the elasticity of the skin covering material 42. In addition, the tackiness of the sealing pad 14 alone can be used to create and maintain the airtight seal or watertight seal with the user's skin 48. Examples of this type of embodiment include a latex glove with a sealing pad 14 associated with the wrist opening to the glove. Another example is a condom FIG. 18 used to isolate the user's penis, or any other covering of an appendage.

Figure 17:
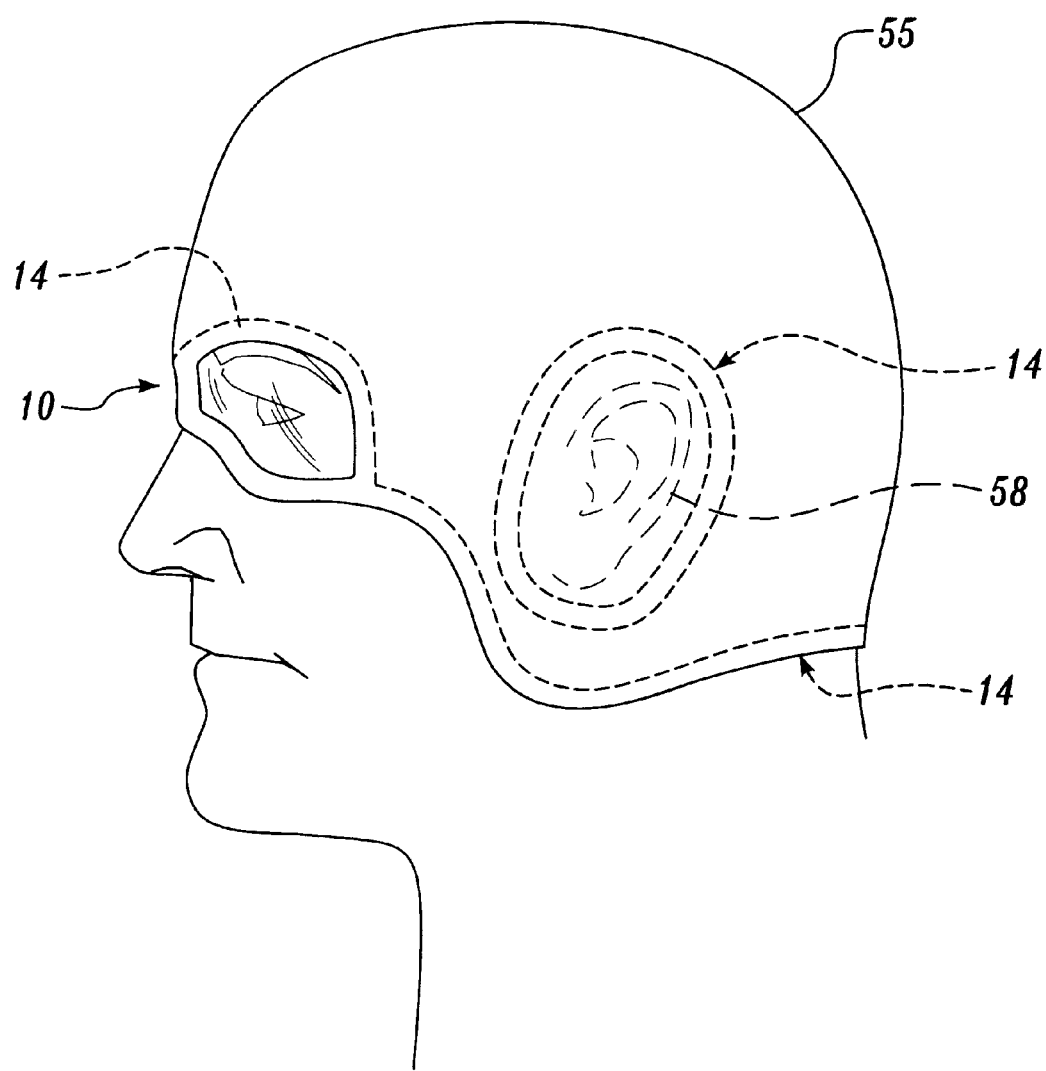
FIG. 17 is a partial pictorial view of a swim cap with incorporated goggles utilizing the present invention

Another example of this embodiment is a seal 14 over or around the ears 58 to prevent water from entering the ear canals. Such a seal can be used alone or as a component of a swim cap 55 as illustrated in FIG. 17. The present invention may also be needed to form a swim cap 55 with integrated goggles 10. Likewise, the sealing pad 14 could be used for the perimeter lining of a shower cap.

In another embodiment shown in FIG. 15 and 16 the skin covering material 42 contains multiple openings with sealing pads 14 at one or more of the openings. The skin covering material 42 can be of various shapes including but not limited to a sleeve-like cylindrical configuration that can be open at one or both ends, with the sealing pad 14 placed at either or both open ends. In one embodiment the sealing pad 14 can be placed on the inside of the open end or ends of the cylindrical sleeve-like garment 53. This sleeve-like garment 53, which can be made of a waterproof material such as plastic, can be slipped over the skin and a fiberglass/plastic cast 52 of an appendage 51 such as an arm or foot. The sealing pads 14 placed at the open end or ends provide a protective waterproof barrier for the cast 52 on an appendage 51 such as an arm or foot. The cast 52 covered by this sleeve-like garment 53 can thus be exposed to or immersed into water such as with taking baths or showers without exposing the cast 52 to water. In this embodiment the outer environment is wet but the inner environment containing the cast 52 remains dry thus protecting the underlying cast 52 and user's skin 48.

The sealing pad 14 can be placed on the interior or exterior surface of the skin covering material 42. For example, the sealing pad 14 can be placed on a flap to form a seal with user's skin 48 or an external outer garment. As shown in FIG. 15 and 16, the sealing pad 14 can be attached to the exterior of the folded over flap on the skin covering material 42, such as the material used in a cast cover 53. The sealing pad 14 can then be covered with a removable protective layer of material 54, such as wax paper, to protect the sealing pad 14 and maintain the tackiness of the sealing pad 14 until it is used. After the user has properly positioned the cast cover 53, the protective layer of material 54 is removed from the sealing pad 14, and the flap is unfolded to bring the sealing pad 14 into contact with the user's skin 48 and form an airtight or watertight seal.

Another embodiment is garment 42 that has multiple openings with a sealing pad 14 affixed to the garment at one or more of the openings. An example is a protective chemical jump suit configured with the sealing pad 14 placed at the openings of the material 42 through which the user's appendages 51 pass. The openings made airtight by the sealing pad 14 can include, but are not restricted to, openings at the neck, the torso, the waist, the arms, hands, legs, the feet, fingers, penis and toes. In another example the appendage covering can be used to isolate bodily fluids and gases that include but not restricted to tears, blood, cerebrospinal fluid, semen, vaginal fluids, mucous, sweat, breath, urine and fecal material. An example of this embodiment is a condom with a sealing pad 14 at its orifice.

Figure 18:
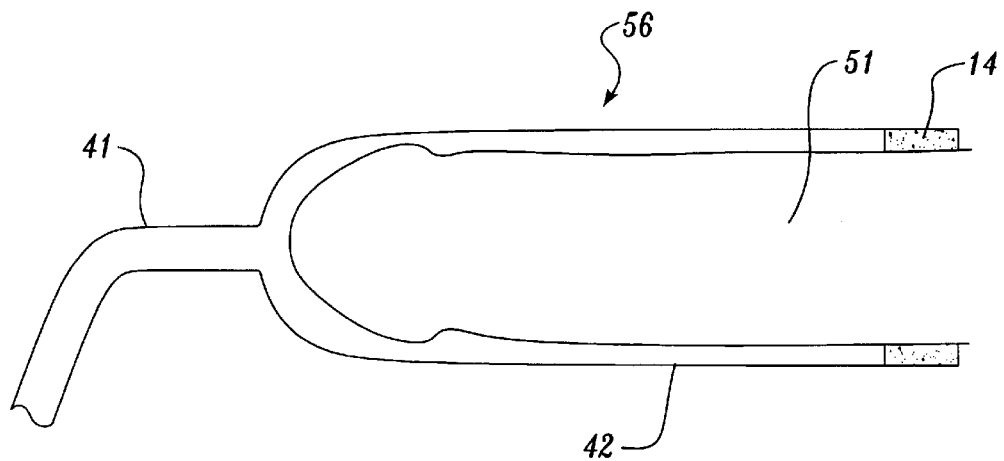
FIG. 18 is a partial pictorial view of a condom catheter with a tube exiting from the skin covering.

In another embodiment the sealing pad 14 can be used with the skin covering material 42 with at least one opening in said skin covering material 42. Said skin covering material 42 may have a tube or conduit 41 attached which transfers fluids, gases, or solids away from the user's skin 48 and body. An example of this embodiment is a condom catheter 56 used to transport urine away from the skin of the penis 51 after micturition as shown in FIG. 18.

Similarly in another example the tube or conduit 41 can transport fluids, gases, or solids or energy toward the skin 48 and body. An example of this embodiment is a tube or conduit 41 that transports oxygen to gangrenous skin 48 of an appendage used to kill anaerobic bacteria. This example isolates the wound serving to keep both said wound sterile and prevent nosocomial infection.

In the preferred embodiment, the plasticizing oil used in gelatinous elastomer 63 is an oil that is biocompatible with use on human skin and non-irritating. In the alternative, the gelatinous elastomer 63 can be readily manufactured so that the plasticizing oil near the surface of the sealing pad in contact with the user's skin 48 contains some desirable compound or material to be applied to the skin. For example, the plasticizing oil can be formed to contain drugs, medicines, nutrients, skin medicinals, or other materials that either can themselves be used as plasticizing agents, are soluble in the plasticizing agent or can be suspended in the plasticizing agent. Examples of such use would be a wound or burn skin covering material 42 or bandage 59.

Figure 19:
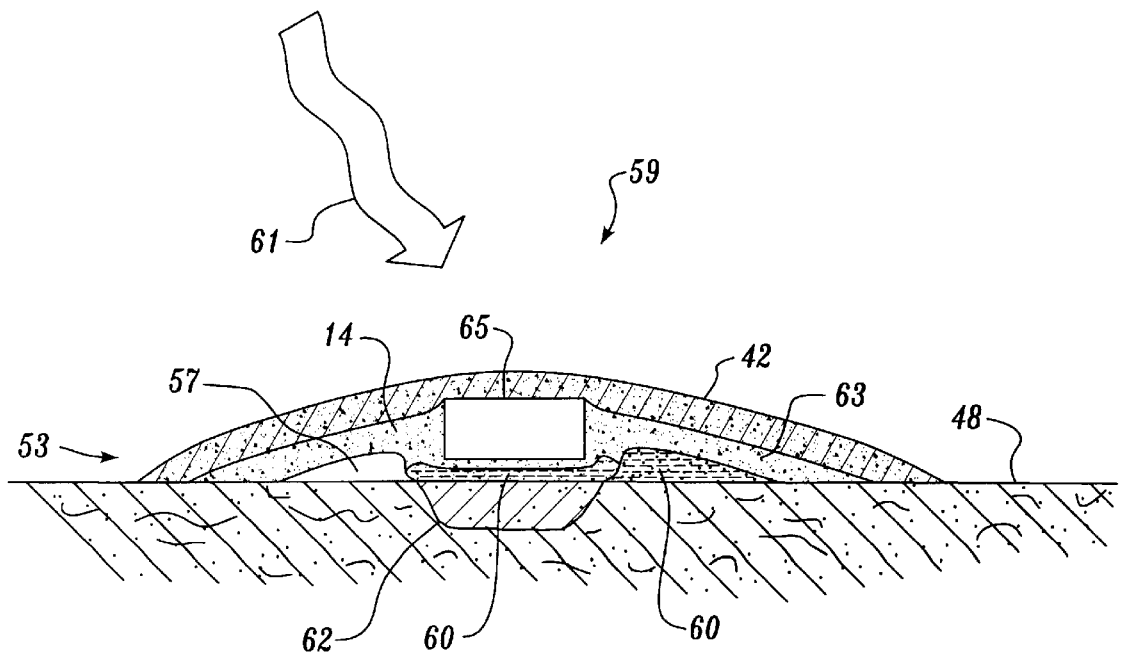
FIG. 19 is a cross section of a bandage with incorporated energy device utilizing the present invention.

In another embodiment, the sealing pad is used to form an air, vapor or water barrier between the user's skin 48, the external environment 58, thus creating an internal space 57. Contained in the sealing pad 14 or in the internal space, such as the internal space 57 between the user's skin 48 and the sealing pad 14 is a gas, solid, liquid or gel substance 60 to be applied to the user's skin 48 for medicinal, skin care, or other purposes. An example of this embodiment is a wound covering such as a bandage 59, where medication 60 to treat or protect the user's skin 48 or the wound 62 is retained on the inside of the sealing pad 14 as illustrated in FIG. 19. The sealing pad 14 is used to isolate the skin's environment such that medication 60 or other products can be applied to the portion of user's skin 48 under the sealing pad. Said medication 60 or other products can be independent of the sealing pad 14 or incorporated into the plasticizing oil used in all or a portion of the sealing pad 14. A tube or other passage may be included to supply, remove, or maintain the medication 60 against the user's skin 48, particularly where the medication is a liquid or gas.

Recent medical research has indicated that various compounds, particularly medicinal compounds, may be more effectively applied to a wound 62 or other areas of the user's skin 48, or transmitted through the user's skin 48, when energy 61 is applied to the user's skin 48, the compound 60, or the means of retaining the compound against the skin. Said energy 61 can include but are not restricted to sound, magnet fields, electricity, electromagnetic energy such as light vibrational energy such as ultrasound, kinetic energy, and heat. It is anticipated that these and numerous other types of energy 61 can be more effectively utilized with the present invention. The present invention FIG. 19 is uniquely situated to enhance the effectiveness of such energy 61. The present embodiment can isolate and maintain a constant environment for a compound 60 on the user's skin 48 or wound 62 during energy 61 delivery. An example shown in FIG. 19 is bandage 59 in which a sealing pad 14 is incorporated into a skin covering material 42 that isolates the wound 62 environment where medication 60 is isolated to the wound region 62 during the administration of the energy 61 from an external source. The wound 62 can include but are not restricted to cancer, diseased skin, a cut, a burn, or a surgical wound.

Another example also shown in FIG. 19 includes an energy source device 65 integrated directly into the sealing pad 14 or skin covering material 42 to form an energy bandage 59. Said energy bandage 59 delivers energy to the user's skin 48 or wound 62. An isolated surface or space 57 is maintained around the user's skin 48 by the sealing pad 14 and the skin covering material 42. Said isolated surface or space 57 is protected from external environmental influences that include but are not restricted to light, heat, drying, moisture, infectious agents and dirt.

Some recent research has also indicated that some types of wounds heal better when there is an energy flowing over the surface or into the wound 62. Another embodiment can include a bandage 59 in which the sealing pad 14 or skin covering material 42 can be formed from a material that either insulates or facilitates surface energy application. In one example this can be accomplished by applying an appropriate voltage across the portion of the sealing pad 14 or skin covering material 42 or wound 62. Another example is a bandage 59 with and energy source device 65 that isolates the wound 62 such that there is limited conduction of electricity to areas beyond the wound's 62 environment. The gelatinous elastomer 63 or added compounds 60 can partially isolate the user from any undesirable effect such as mechanical irritation of the energy source device 65, the energy 61 or the medication 60. In another example the sealing pad 14 of the present invention may also be used to apply energy or measure energy within the isolated space 57 or the wound 62 or the user's skin 48.

In another embodiment also shown in FIG. 19 the gelatinous elastomer 63 of the sealing pad 14 or the skin covering material 42 can maintain the energy source device 65 in a fixed location or locations relative to the compound 60 and the portion of the user's skin 48 or wound 62 to which the compound 60 is applied.

Another embodiment of the sealing pad 14 can include a sealing pad 14 that does not completely enclose a portion of the user's skin 48. Examples of such non-annular seals include a linear barrier, an open ring or any other shape that does not form a closed annular ring. Such a non-annular sealing pad 14 only partially isolates any portion or portions of the user's face 46 or user's skin 48 from the outside environment.

Figure 20:
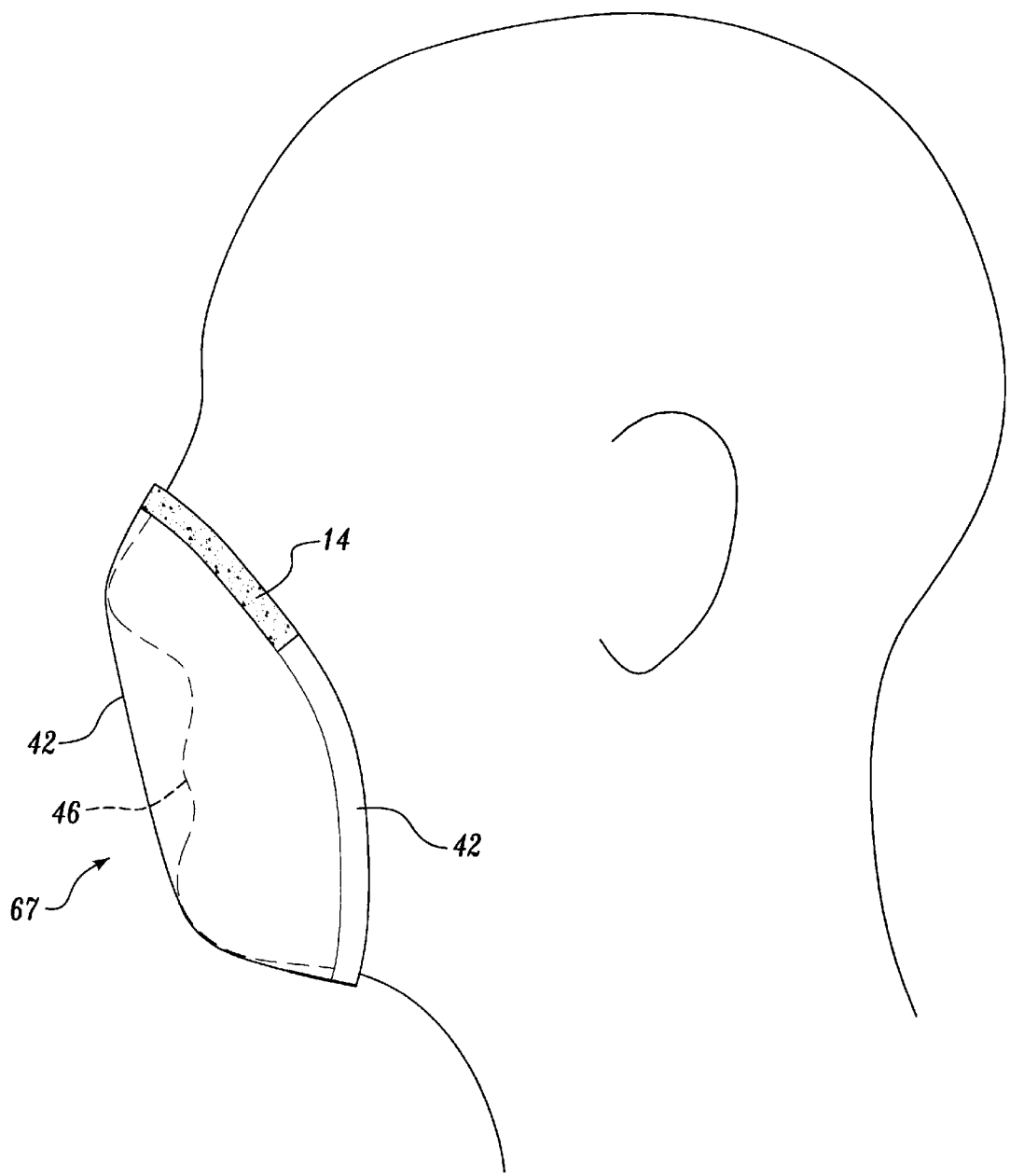
FIG. 20 is a partial view of a surgical mask utilizing the present invention.

Either the closed annular or non-annular sealing pad 14 can also be used with a skin covering material 42 that is not absolutely airtight or watertight, to include but not restricted to cloth, paper, leather or Gore-Tex. The sealing pad 14 thus utilized serves as a barrier that prevents or restricts the transmission of air, water, or other materials towards or away from the user's skin 14 under the skin covering material 42, except to the extent permitted by the skin covering material 42 and any open areas of the sealing pad. An example illustrated in FIG. 20 uses a non-annular sealing pad 14 to form a partial air, vapor or water barrier between the user's skin 48 and the outer environment. In this embodiment the skin covering material 42 is a piece of permeable or semipermeable material. An example is a surgical or air filtration mask 67 with the sealing pad 14 located at the nose bridge. When the user breathes through the mask, the moist air from the breath is impeded from rising upward by the sealing pad 14, thus preventing or inhibiting moist air from traveling towards the user's eyes. This can be important if the user wears eyeglasses since the eyeglasses tend to become fogged up with normal surgical masks due to the warm moist air rising from the perimeter of the mask.

In another embodiment the sealing pad 14 can partially isolate a human orifice, such as the mouth, the nose, the ears, the eyes, the urethra, the vagina, or the rectum. The sealing pad 14 can be used to isolate, partition, or alter the direction of flow of bodily fluids and gases that include but are not restricted to tears, blood, cerebrospinal fluid, semen, vaginal fluids, mucous, sweat, breath, urine and fecal material. An example of this embodiment is a sealing pad 14 of the present invention that can form a watertight seal between a pair of infant or toddler diapers and the outside environment, thereby preventing leakage.

In another embodiment the sealing pad 14 is a continuous sheet. Said sealing pad 14 alone can serve as a complete covering of the skin or a human orifice, such as the mouth, the nose, the ears, the eyes, the urethra, the vagina, or the rectum. The sealing pad 14 can be used to isolate, partition, or alter the direction of flow of bodily fluids and gases that include but are not restricted to tears, blood, cerebrospinal fluid, semen, vaginal fluids, mucous, sweat, breath, urine and fecal material. An example of this embodiment are gel sealing pad 14 ear covering to prevent water or blood from entering the ear during surgery. Other examples of such use would be the use of a sealing pad 14 configured as a thin sheet containing medicine to be used as a burn covering or bandage 59. Likewise, the sealing pad 14 could be used for soundproofing or enhancement such as underwater headphones.

Figure 21:
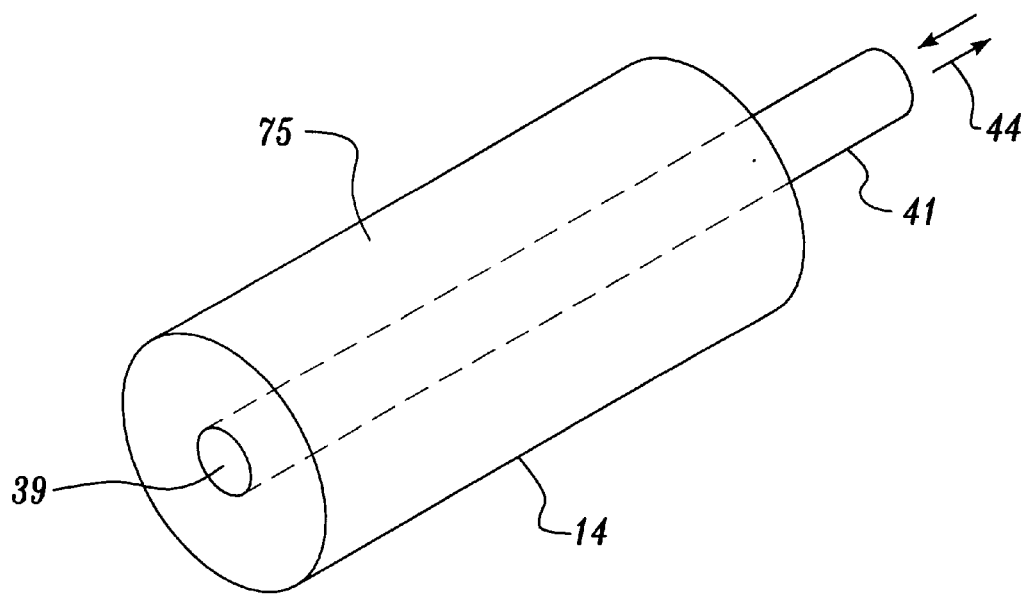
FIG. 21 is a partial view of a nose plug containing a central conduit.

The sealing pad 14 of the present invention can be configured as a plug shown in FIG. 21 to be used to create a seal within a body cavity or orifice. The present invention may be used as earplugs, either for swimming or to apply medicine to the inner ear or external auditory canal ear. In another example the sealing pad 14 of the present invention can be used as a nose plug to occlude the nostrils. When used as the nose plug, the sealing pad 14 may also be impregnated with medicines that help stop nosebleed.

Figure 24:
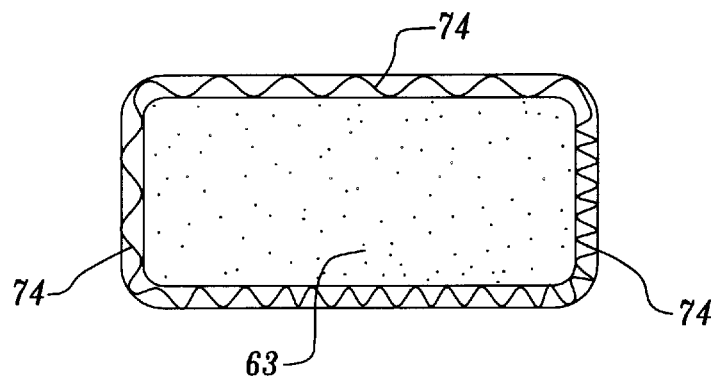
FIG. 24 is a cross section showing a method for modifying the physical properties of a gelatinous elastomer comprising the integration of a second material into the gelatinous elastomer utilizing a exoskeleton.

In another embodiment illustrated in FIG. 24 the nose plug can be hollow opening 39 or contain a tube 55 that delivers or facilitates the delivery of solid, gaseous or liquid materials 44 that includes but are not restricted to scents, aromas, gasses, fluids, medicines, medicinals, and powders.

The sealing pad 14 of the present invention can be used internally within the body to protect a surgical field. It can be designed to isolate, either partially or completely, any portion or portions of the skin or the membrane of a body part. An example of this embodiment is a surgical covering that prevents the spillage of cancer cells into the abdominal or pelvic cavity during the removal of a cancerous tumor attached to a body part such as the ovary.

Presently gelatinous elastomers 63 do not attach well by standard methods (such as glues or ties or straps) to other materials such as the skin covering material 42. The gelatinous elastomer 63 tears easily and does not bond well to other flat surfaces. This has limited the practical and routine application of the gelatinous elastomer technology and manufacturing. The present invention is also designed to solve this attachment problem.

The gelatinous elastomer 63 of the present invention can be attached to the skin covering material 42 or a transitional material 72 in numerous manners. For example, mechanical fasteners, glues, or adhesives can be used to attach a sealing pad 14 to a skin covering material. In addition, the gelatinous elastomer 63 may be wholly or partially surrounded by a flexible film 24 that is then attached to the skin covering material 42.

Figure 22:
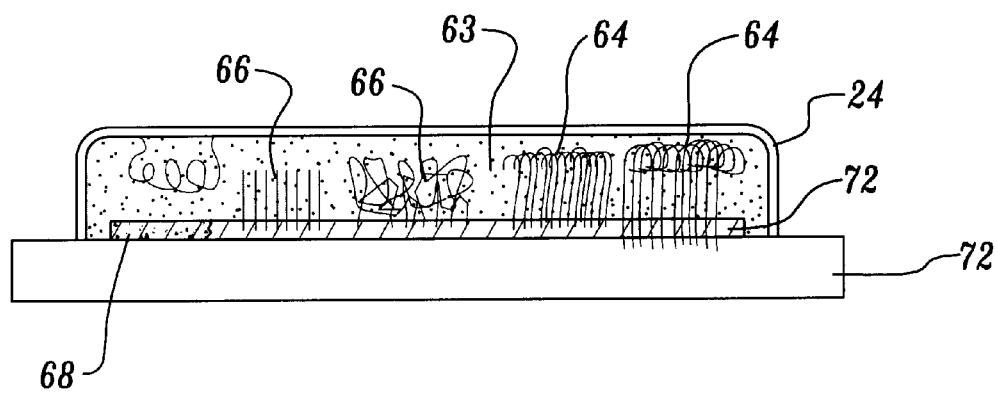
FIG. 22 is a cross section showing a method of attachment utilizing the present invention.
Figure 23:
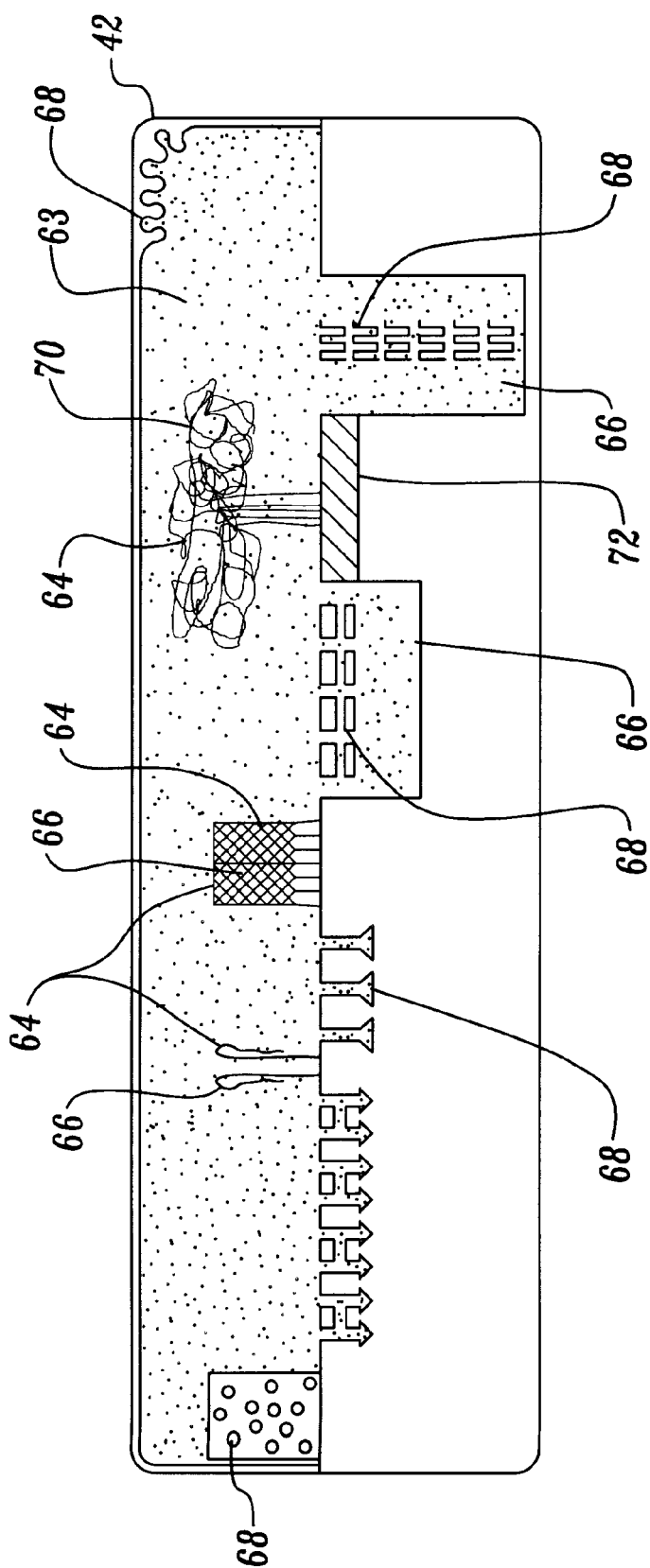
FIG. 23 is a cross section showing examples of the attachment method utilizing the present invention.

The present invention provides for an alternative and preferable method of attachment for fastening the gelatinous elastomer 63 to the skin covering material 42, a transitional material 72, or other material. Referring to FIG. 22 the skin covering material 42 can be more intimately bound to the sealing pad 14 by imbedding the gelatinous elastomer 63 of the sealing pad 14 into a large plurality of interstices or interstitial spaces 66 in the skin covering material 42 or a transitional material 72. Such integration substantially increases the contact surface area between the gelatinous elastomer 63 and the skin covering material 42 or transitional material 72 often by orders of magnitude, and also may take advantage of the preferential self-bonding of the gelatinous elastomer 63 to itself as it surrounds portions of the skin covering material 42 or the transitional material 72. The sealing pad 14 can also be attached to the skin covering material 42 by integrating the gelatinous elastomer 63 of the sealing pad 14 into a large plurality of projections 64. Said projections can include but are not restricted to a woven or random network of threads or other fabric 70 attached to or part of the skin covering material 42 or of the transitional material 72 as illustrated in FIGS. 19 and 22. The threads can be made of various materials to include natural fibers such as wool or cotton or man-made fibers such as nylon. These woven fibers form interstitium 66 into which the sealing pad 14 is integrated. The sealing pad 14 can also be intimately bound to the skin covering material 42 or to the transitional material 72 by integrating a large plurality of projections 64 or voids 68 from the skin covering material 42 or from the transitional material 72 into the sealing pad 14 as illustrated in FIG. 22. These voids 68 can include, but are not restricted to channels, perforations, holes, loops, indentations and spaces and said voids 68 can form interstitium 66 into which the sealing pad 14 is integrated.

The skin covering material 42 and the transitional material 72 can be defined to include, but are not restricted to include the frame, the mask, the goggles, the protective clothing, the cast cover and other structures. The skin covering material 42 and the transitional material 72 can be formed from the same or different material and may have similar or different physical properties. The skin covering material 42 and the transitional material 72 can be continuous, attached or separate.

When the gelatinous elastomer 63 is integrated into a plurality of interstitium 66 in the skin covering material 42 itself or some other transitional material 72, these interstitium 66 are preferably small spaces or voids 68 that are filled by the gelatinous elastomer 63. In one embodiment of this method, the gelatinous elastomer 63 is made to flow more readily than it would be during its normal use by heating or melting the gelatinous elastomer 63 or by waiting to add a solidifying catalyst, or by other methods commonly known in the industry. While the gelatinous elastomer 63 is in this less viscous state, it is integrated into the interstitium 66 of the skin covering material 42 or transitional material 72. In one alternative, illustrated in FIG. 22, a surface of the skin covering material 42 or other transitional material 72 to which the sealing pad 14 will be attached is configured to create a larger plurality or array of interstitium 64, 66, 68, 70 near the surface of the material. Preferably, the dimensions of the interstitium are normally less than 3 millimeters, but are not necessarily restricted to less than 3 millimeters. Said interstitium 66 preferably are interconnected to take advantage of internal bonding of the gelatinous elastomer 63. Examples of such configurations FIG. 22 would include voids 68 or projections 64 in the skin covering material 42 or transitional material 72. Said intermediate transitional material 72 can include but is not restricted to a fabric, an elastic bandage, either the hook or loop portion of a traditional VELCRO® fastener, a piece of foam, or other commonly known materials having a large plurality of interstitium. The gelatinous elastomer 63 of the sealing pad 14 is then integrated into the voids 68 or projections 64 that form interstitium 66. For example, the gelatinous elastomer 63 can be made more liquid or less viscous than it would be during its normal use (through, for example, melting the gelatinous elastomer 63 of the sealing pad 14) and then be poured or molded into the interstitium 66 on the surface the skin covering material 42 or transitional material 72. Likewise, the gelatinous elastomer 63 can be integrated with the interstitium 66 of the skin covering material 42 or transitional material 72 by the application of pressure or other methods.

The use of a large plurality of small interstitium 66 for attaching the sealing pad 14 to the skin covering material 42 or transitional material 72 allows for a vast array of new applications of gelatinous elastomer sealing pads 14. For example, referring to FIG. 19, the gelatinous elastomer sealing pad 14 can be liquefied through heating the material to its melting point, and then the material can be poured or molded into the transitional material 72 which can be an elastic fabric 72 used in a traditional rolled elastic bandage, resulting in an elastic material that can be stretched significantly and still form a watertight seal with the user's skin 48. Such an example of an elastic bandage is Coban®. In addition, the elastic bandage so formed will form a watertight seal with itself where it overlaps, and thus can be used to form a watertight wrap around the user's arm, a cast, or other locations where it is desirable to isolate a portion of the user's skin 48 from the outside environment. In addition, if a relatively soft and biocompatible gelatinous elastomer is used, then the elastic wrap can be used to position material, medication 60, medical devices, or sensors against the user's skin 48 for long periods of time without inducing discomfort or an adverse reaction from the user.

Another example of the preferred method of attachment would be to pour or mold the liquid gelatinous elastomer 63 onto a transitional material 72 such as the loop side of a traditional VELCRO® fastener. The sealing pad 14 can then be attached to other objects using any of the conventionally available methods for attaching a VELCRO® fastener such as adhesives, sewn stitches, or fasteners.

In another embodiment the sealing pad 14 can be constructed with a varying gradient of hardness or softness. One example would be a sealing pad 14 on a respiratory or breathing mask 40 in which the portion of the pad nearest the skin is softer than the portion of the sealing pad 14 away from the user's skin 48. This would allow the sealing pad 14 to be soft as it approximates the user's skin 48 of the user's face 46 while remaining firm at its attachment to the mask's frame 40.

An exoskeleton 74 shown in FIG. 24 can be used to substantially alter and control the physical properties of the gelatinous elastomer 63, making it softer, harder, more tear resistant, stronger, more or less elastic, or more or less resilient, especially near the surface. The skin covering material 42 or other material 72 may be configured to form an exoskeleton 74 for the sealing pad 14 as illustrated in FIG. 19. The exoskeleton 74 can have a pattern which consists of but is not restricted to an ordered or random pattern, and said patterns can be but are not restricted to channels, mesh, or fibers. Preferably, the exoskeleton consists of a porous material into which the gelatinous elastomer 63 is integrated. An example of such configuration would include lining the surface of the mold with a porous material and pouring or injecting the melted gelatinous elastomer 63 into the mold, and allowing the elastomer to harden. While the gelatinous elastomer 63 is melted, it would integrate into the interstitium 66 of the porous material and be well bonded to the porous material after it has hardened. The exoskeleton 74 may vary in its pattern, thickness and uniformity, but its variation is not restricted to these characteristics. The exoskeleton can arise from or be attached to the skin covering material 42 or transitional material 72. The exoskeleton may, if desirable, be covered by or attached to a surface membrane.

Figure 25:
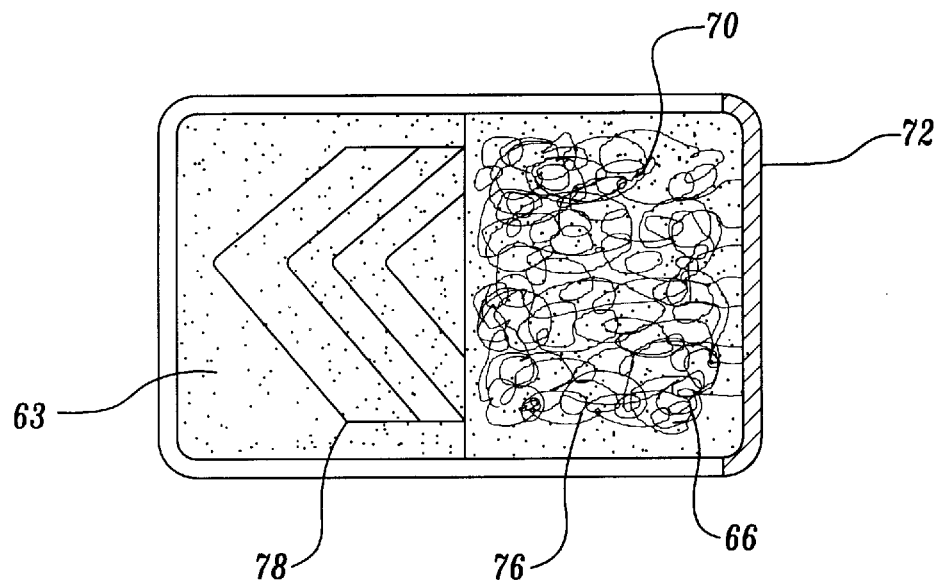
FIG. 25 is a cross section showing a method for modifying the physical properties of a gelatinous elastomer comprising the integration of a second material into the gelatinous elastomer utilizing an endoskeleton.

An endoskeleton 76 shown in FIG. 25 can also be used to substantially alter and control the physical properties of the gelatinous elastomer 63, making it softer, harder, more tear resistant, stronger, more or less elastic, or more or less resilient, especially internally. In the embodiment shown in FIG. 25, the projections 64 and interstitium 66 can create an endoskeleton 76 inside the gelatinous elastomer sealing pad 14. The endoskeleton 76 can have a pattern which consists of but is not restricted to an ordered or random pattern, and said patterns can be but are not restricted to channels, mesh, or fibers. For example an endoskeleton 76 would preferably be formed from projections 64 or fibers that extend substantially throughout the sealing pad 14 as shown in FIG. 25. Such endoskeleton 76 can be used to gently bond the gelatinous elastomer 63 sealing pad 14 to virtually any material. Said material can be attached to or can be separate from the skin covering material 42 or transitional material 72. The endoskeleton 76 can also be used to alter the physical properties of the gelatinous elastomer 63 sealing pad 14, as described with the exoskeleton structure 74. In addition, the endoskeleton 76 can be used to vary the physical properties of the gelatinous elastomer 63 with various regions of the gelatinous elastomer 63, altering, for example, the force vs. deflection characteristics of the gelatinous elastomer 63 at one region of the endoskeleton 76 versus another region of the endoskeleton 78. The endoskeleton 76 can be separate from the skin covering material 42 or transitional material 72 as shown in FIG. 25.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A sealing pad forming a substantially airtight seal between a skin covering material and at least a portion of the user's skin comprising:
   a compliant and resiliently deformable annular gelatinous elastomer suitable to conform under pressure to form a substantially airtight seal between the skin covering material and at least a portion of the user's skin.

2. The sealing pad of claim 1, wherein the sealing pad forms a substantially airtight seal between the user's skin and the effective perimeter of the skin covering material.

3. The sealing pad of claim 1, further comprising a flexible membrane attached to the skin covering material and also attached to the sealing pad by surrounding and enclosing the sealing pad.

4. The sealing pad of claim 1, wherein the skin covering material has a large plurality of interstitium and wherein the sealing pad is attached to the skin covering material by integrating the sealing pad into such interstitium.

5. The sealing pad of claim 4, wherein the skin covering material has hooked projections and wherein the sealing pad is attached to the skin covering material by integrating the sealing pad within the interstitium of the hooks.

6. The sealing pad of claim 1, further comprising a transitional material attached to the skin covering material and having a large plurality of interstitium, wherein the gelatinous elastomer of the sealing pad is integrated into such interstitium in order to attach the gelatinous elastomer to the transitional material.

7. The sealing pad of claim 6, further comprising a transitional material attached to the skin covering material and having hooked projections, wherein the gelatinous elastomer of the sealing pad is integrated into said hooked projections and wherein the sealing pad is attached to the transitional material by integrating the sealing pad within the interstitium of the hook.

8. The sealing pad of claim 1, wherein:
   the sealing pad is attached to a substantially waterproof covering material designed to cover an appendage of the user and having at least one opening for insertion of the user's appendage; and
   the sealing pad forms a substantially watertight seal between the covering material and the user's skin at at least one of the openings.

9. The sealing pad of claim 1, wherein the sealing pad is configured to form an airtight seal with the user's skin at least partially isolating at least one of the user's orifices from the outside environment.

10. The sealing pad of claim 9, wherein the sealing pad is attached to a lightweight skin covering material that is substantially permeable to vapor, but will effectively prevent the transmission of solids or liquids.

11. The sealing pad of claim 10 configured to at least partially isolate the user's nose and mouth.

12. The sealing pad of claim 11 wherein the sealing pad and skin covering material are used as a surgical mask.

13. The sealing pad of claim 9 configured to form an airtight seal fully isolating the user's orifice from the outside environment.

14. The sealing pad of claim 13, wherein the sealing pad and skin covering material are used as a breathing mask.

15. The sealing pad of claim 1, wherein the sealing pad is configured as a bandage to at least partially isolate a wound or injury of the user from the outside environment.

16. The sealing pad of claim 1, wherein the pliability of the sealing pad varies between the user's skin and the skin covering material.

17. A sealing pad forming a substantially airtight seal between a skin covering material and at least a portion of the user's skin comprising:
   a compliant and resiliently deformable gelatinous elastomer which form a non-annular barrier suitable to conform under pressure to form a substantially airtight seal between the skin covering material and at least a portion of the user's skin.

18. The sealing pad of claim 17, further comprising a flexible membrane attached to the skin covering material and also attached to the sealing pad by surrounding and enclosing the sealing pad.

19. The sealing pad of claim 17, wherein the skin covering material has a large plurality of interstitium and wherein the sealing pad is attached to the skin covering material by integrating the sealing pad into such interstitium.

20. The sealing pad of claim 19, wherein the skin covering material has hooked projections and wherein the sealing pad is attached to the skin covering material by integrating the sealing pad within the interstitium of the hook.

21. The sealing pad of claim 17, further comprising a transitional material attached to the skin covering material and having a large plurality of interstitium, wherein the gelatinous elastomer of the sealing pad is integrated into such interstitium in order to attach the gelatinous elastomer to the transitional material.

22. The sealing pad of claim 21, further comprising a transitional material attached to the skin covering material and having hooked projections, wherein the gelatinous elastomer of the sealing pad is integrated into said hooked projections and wherein the sealing pad is attached to the transitional material by integrating the sealing pad within the interstitium of the hook.

23. The sealing pad of claim 17, wherein:

the sealing pad is attached to a substantially waterproof covering material designed to cover an appendage of the user and having at least one opening for insertion of the user's appendage; and the sealing pad forms a substantially watertight seal between the covering material and the user's skin at at least one of the openings.

24. The sealing pad of claim 17, wherein the sealing pad is configured to form an airtight seal with the user's skin at least partially isolating at least one of the user's orifices from the outside environment.

25. The sealing pad of claim 24, wherein the sealing pad is attached to a lightweight skin covering material that is substantially permeable to vapor, but will effectively prevent the transmission of solids or liquids.

26. The sealing pad of claim 25 configured to at least partially isolate the user's nose and mouth.

27. The sealing pad of claim 26, wherein the sealing pad and skin covering material are used as a surgical mask.

28. The sealing pad of claim 17, wherein the pliability of the sealing pad varies between the user's skin and the skin covering material.

29. A device for delivery of a compound to a portion of the user's skin; and a means for utilizing an energy source to aid in the delivery of the compound to the user's skin comprising:

a gelatinous elastomer configured to isolate the portion of the user's skin and maintain the compound against such portion of the skin.

30. The delivery device of claim 29, wherein the energy source supplies electrical energy.

31. The delivery device of claim 29, wherein the energy source supplies magnetic energy.

32. The delivery device of claim 29, wherein the energy source supplies vibrational energy.

33. The delivery device of claim 29, wherein the energy source supplies electromagnetic energy.

34. The delivery device of claim 29, further comprising a passage to supply, remove, or maintain the compound against such portion of the skin.

35. A method for attaching a gelatinous elastomer to a second material comprising:

forming a large plurality of interstitium at the location on the second material where the gelatinous elastomer will be attached; and integrating the gelatinous elastomer into such interstitium.

36. The method of claim 35, wherein the interstitium are derived from a large plurality of projections from the surface of the second material.

37. The method of claim 36, wherein the second material comprises a fabric material and the gelatinous elastomer is integrated at least partially into the fabric-like portion of the second material.

38. The method of claim 36, wherein the projections from the second material are hooked.

39. The method of claim 35, wherein the interstitium comprise a large plurality of small voids in the second material.

40. The method of claim 39, wherein the second material comprises a fabric material and the gelatinous elastomer is integrated at least partially into the fabric-like portion of the second material.

41. The method of claim 39, wherein the voids of the second material are interconnected channels.

42. A method for modifying the physical properties of a gelatinous elastomer comprising the integration of a second material into the gelatinous elastomer near the surface of the gelatinous elastomer to form an exoskeleton for the gelatinous elastomer that alters the physical properties of the gelatinous elastomer.

43. The method of claim 42, wherein the second material is a fabric material.

44. The method of claim 42, wherein the exoskeleton has an ordered pattern.

45. The method of claim 42, wherein the exoskeleton has a random pattern.

46. A method for modifying the physical properties of a gelatinous elastomer comprising the integration of a second material into the gelatinous elastomer, wherein the second material is integrated into a substantial portion of the interior of the gelatinous elastomer to form an endoskeleton for the gelatinous elastomer that alters the physical properties of the gelatinous elastomer.

47. The method of claim 46, wherein the endoskeleton is varied within the gelatinous elastomer in order to create a plurality of regions within the gelatinous elastomer having different physical properties.

48. The method of claim 46, wherein the second material is a fabric material.

49. The method of claim 46, wherein the endoskeleton has an ordered pattern.

50. The method of claim 46, wherein the endoskeleton has a random pattern.

51. The method of claim 46, further comprising integrating a third material into the gelatinous elastomer to form an exoskeleton which alters the physical properties of the gelatinous elastomer.

\* \* \* \* \*

UNITED STATES PATENT AND TRADEMARK OFFICE
CERTIFICATE OF CORRECTION

PATENT NO.    : 6,152,137
DATED         : November 28, 2000
INVENTOR(S)   : Alan N. Schwartz and Thomas D. Theisen It is certified that error appears in the above-identified patent and that said Letters Patent is hereby corrected as shown below:

Column 17,
Line 37-43, amend Claim 29 to read as follows:

-- A device for delivery of a compound to a portion of the user's skin comprising:
a gelatinous elastomer configured to isolate the portion of the user's skin and maintain the compound against such portion of the skin; and
a means for utilizing an energy source to aid in the delivery of the compound to the user's skin. --

Signed and Sealed this

Twenty-seventh Day of November, 2001

*Attest:*

NICHOLAS P. GODICI
*Attesting Officer*   Acting Director of the United States Patent and Trademark Office